United States Patent

Bortinger et al.

Patent Number: 5,521,134
Date of Patent: May 28, 1996

[54] METHOD FOR REGENERATING VANADIUM/PHOSPHORUS OXIDATION CATALYSTS

[75] Inventors: Arie Bortinger, Ridgewood, N.J.; Michael Bruscino, Washingtonville, N.Y.

[73] Assignee: Scientific Design Company, Inc., Little Ferry, N.J.

[21] Appl. No.: 506,593

[22] Filed: Jul. 25, 1995

Related U.S. Application Data

[63] Continuation of Ser. No. 199,528, Feb. 22, 1994, abandoned.

[51] Int. Cl.⁶ .............. B01J 20/34; B01J 38/40; C07D 307/89
[52] U.S. Cl. .............. 502/39; 502/38; 502/51; 502/52; 502/209; 502/210; 549/259; 549/260
[58] Field of Search .............. 502/52, 38, 39, 502/51, 209, 210; 549/259, 260

[56] References Cited

U.S. PATENT DOCUMENTS

| | | | |
|---|---|---|---|
| Re. 30,430 | 4/1980 | Kerr | 260/396.25 |
| 3,474,041 | 10/1969 | Kerr | 252/411 |
| 3,901,933 | 8/1975 | Norton | 558/329 |
| 3,906,008 | 9/1975 | Ueeda | 260/346.8 A |
| 4,020,174 | 4/1977 | Partenheimer | 260/346.8 A |
| 4,081,460 | 3/1978 | Kerr et al. | 260/346.75 |
| 4,089,807 | 5/1978 | Partenheimer | 252/415 |
| 4,094,816 | 6/1978 | Partenheimer | 252/415 |
| 4,111,832 | 9/1978 | Rohbock et al. | 252/412 |
| 4,324,648 | 4/1982 | Roberts et al. | 208/114 |
| 4,448,978 | 5/1984 | Mount et al. | 549/259 |
| 4,460,784 | 7/1984 | Harju et al. | 549/259 |
| 4,515,899 | 5/1985 | Click et al. | 502/35 |
| 4,596,878 | 6/1986 | Click et al. | 549/249 |
| 4,791,080 | 12/1988 | Gruber et al. | 502/52 |
| 5,011,945 | 4/1991 | Taheri | 549/260 |
| 5,021,588 | 6/1991 | Contractor | 549/259 |
| 5,070,608 | 12/1991 | Barone | 502/209 |
| 5,071,802 | 12/1991 | Shimizu et al. | 502/38 |

FOREIGN PATENT DOCUMENTS

| | | |
|---|---|---|
| 0123467 | 10/1984 | European Pat. Off. . |
| 1439489 | 6/1976 | United Kingdom . |
| 1464198 | 9/1977 | United Kingdom . |

*Primary Examiner*—Sharon Gibson
*Attorney, Agent, or Firm*—Kenneth H. Johnson

[57] ABSTRACT

A method of regenerating V/P/O oxidation catalyst used for the partial oxidation of n-butane which comprises terminating the n-butane feed and contacting the catalyst with an oxygen containing gas, such as air for a sufficient period of time to regenerate the catalyst such that when the n-butane feed is restarted the yield is greater than just before the treatment.

8 Claims, No Drawings

METHOD FOR REGENERATING VANADIUM/PHOSPHORUS OXIDATION CATALYSTS

This application is a continuation of application Ser. No. 08/199,528, filed Feb. 22, 1994 abandoned.

BACKGROUND OF THE INVENTION

The present invention relates to a method for regenerating vanadium-phosphorus-oxygen (VPO) catalysts used in the partial oxidation of hydrocarbons to prepare dicarboxylic acids and anhydrides.

It is known that VPO catalysts produce high yields of dicarboxylic anhydrides by partial oxidation of hydrocarbons. It has been found that the yield of product diminishes with time due to a reduction in the selectivity of the catalyst. Various theories of the reason and methods for overcoming the loss in selectivity of catalyst in situ have been devised.

U.S. Pat. Nos. 3,296,282 and 3,474,041, issued to Ralph O. Kerr, disclose that the VPO catalyst may be regenerated and stabilized by adding specified organophosphorus compounds to the catalyst. The organophosphorus compound may be added with or without the hydrocarbon, either intermittently or continuously. It was found that during the use of the catalysts a portion of the phosphorus is removed from the catalyst, thereby disrupting the initial ratio of P:V in the catalyst, and the added phosphorus compound replaced a portion of the lost phosphorus to thereby maintain the catalyst close to its original selectivity and extending the useful life of the catalyst. A similar approach was disclosed in British Patent Specification 1,291,354 and U.S. Pat. Nos. 3,906,008 and 3,975,407.

Another approach to the same problem, i.e., the disruption of the ratio of P to V by phosphorus loss in the catalyst, is the removal of some of the vanadium. A process using this method is disclosed in U.S. Pat. Nos. 4,020,174; 4,090,807 and 4,094,816 issued to Partenheimer. The use of various organic and inorganic halogen compounds are disclosed to regenerate the catalyst. After treatment with alkyl halides, the patents suggest a steam treatment to cause a water gas reaction to remove residual carbon deposited by the alkyl halide.

U.S. Pat. No. 4,111,832 discloses the use of aqueous ammonia and/or amine to at least partially dissolve the catalyst and thereafter redepositing the catalytic components from the solution.

British Patent Specification 1,464,198 discloses the regeneration of VPO oxidation catalysts by the addition of alkyl esters of orthophosphoric acid and European Patent 123,467 using the same type compounds to reactivate the VPO catalysts.

British Patent Specification 1,439,489 discloses the regeneration of VPO catalyst with a reducing agent such as hydrogen, carbon monoxide, methane or hydrogen sulfide.

U.S. Pat. Nos. 4,515,899 and 4,596,878 disclose regeneration of VPO catalysts and life extension by phosphorus compound treatment followed by steam treatment. The steam was believed to redistribute the deposited phosphorus compounds throughout the bed.

Each of these prior art methods may either require multiple steps such as phosphorus/steam treatment, adding or removing catalyst components or otherwise carrying out relatively complicated in situ operation.

The terms "regenerate" and "reactivate" have been used in the prior art to describe various results from the various treatments. The term "regeneration" is used herein to mean that a higher yield of product is obtained after treatment. The treatment may reduce the activity (the term "activity" as used herein, means the ability of the catalyst to convert hydrocarbon at a given temperature) of the catalyst while improving the selectivity. The overall result is that a higher yield (conversions×selectivity) is obtained, surprisingly without a commensurate increase in bed temperatures usually associated with the prior art methods.

An advantage of the present invention is that substantial improvement in the yield can be obtained without any added activator such as phosphorus compounds. Also this improved yield is obtained without an increase in the temperature of the reaction after treatment. It is an advantage of the present invention that regeneration of the VPO catalyst is obtained without the introduction of any extraneous material into the reaction system. It is a further advantage that the regeneration is obtained using available cheap material.

SUMMARY OF THE INVENTION

The present invention is a method of regenerating a vanadium/phosphorous mixed oxide oxidation catalyst which has declined in activity by treating the catalyst with a stream of oxygen containing gas in the absence of hydrocarbon for a sufficient duration to regenerate the catalyst. The regeneration is preferably carried out in situ in a reactor by terminating the flow of hydrocarbon and passing the gas, e.g. air over the catalyst at temperatures generally in the range used for the reaction, i.e., about 350° to 450° C., preferably 400° to 430° C. for 1 to 48 hours preferably about 3 to 10 hours. The amount of oxygen in the gas stream is preferably in the range of 0.1 to 100 vol. %. The other gas components are inert. The treatment may also be carried out in the absence of steam and any other promoter or activator, although the gas stream may have some intrinsic moisture and small amounts of steam, e.g. from 0.1 to 5 vol. % steam.

The regeneration has been completed when the yield of the catalyst in the oxidation reaction is greater after the treatment than before. After the regeneration step the catalyst activity is about the same as prior to the regeneration step. However, the selectivity is increased which results in a higher maleic anhydride yield. It is believed the increase in selectivity indicates that during the regeneration step catalytic sites responsible for formation of carbon oxides have been reduced which in turn lead to an increase in the selectivity for partial oxidation to maleic anhydride, which may be due to the restructuring of the V/P/O phases or to other phenomena such as redistributions of the promoters.

DETAILED DESCRIPTION AND PREFERRED EMBODIMENTS

Basically, all of the methods used to prepare oxidation catalysts seek to obtain vanadium in a valence state of less then +5. One method of achieving this is to begin with vanadium in less than the +5 valence state.

In another method the catalyst is prepared by precipitating the metal compounds, either with or without a carrier, from a colloidal dispersion of the ingredients in an inert liquid. In some instances the catalyst may be deposited as molten metal compounds onto a carrier. The catalysts have also been prepared by heating and mixing anhydrous forms of phosphorus acids with vanadium compounds and other components.

Another method and that used most widely in the art is to start with vanadium in the +5 state and reduce the valency to less than +5. Several variations on this method have been used to obtain these catalyst. In one method $V_2O_5$ is reduced in a solution with HCl to obtain vanadyl chloride. A typical catalyst preparation may involve dissolving the vanadium, phosphorus, and other components in a common solvent. The reduced vanadium with a valence of less than 5 is obtained by initially using a vanadium compound with a valence of plus 5 such as $V_2O_5$ and thereafter reducing to the lower valence with, for example, hydrochloric acid during the catalyst preparation to form the vanadium oxysalt, vanadyl chloride, in situ. The vanadium compound is dissolved in a reducing solvent, such as hydrochloric acid reduces the valence of the vanadium compound to a valence of less than 5 and functions as a solvent for the reaction. Preferably, the vanadium compound is first dissolved in the hydrochloric acid and thereafter the phosphorus and other components, if any, are added. The reaction to form the complex may be accelerated by the application of heat. The complex formed is then, without a precipitation step, deposited as a solution onto a carrier and dried. Generally, the average valence of the vanadium will be between about plus 2.5 and 4.6 at the time of deposition onto the carrier.

U.S. Pat. Nos. 4,043,943; 4,105,586; 4,251,390; 4,283,307; and 4,418,003 obtain vanadyl chloride for the preparation of the vanadium/phosphorus oxidation catalyst by the reduction of $V_2O_5$ in alcoholic HCl solution, generally referred to as the "anhydrous process" of reducing vanadium to prepare the basic vanadium/phosphorus catalyst. The catalysts produced by this latter method have been found to be generally superior to similar catalyst by the other methods.

U.S. Pat. No. 4,147,661 discloses high surface area VPO mixed oxide catalyst additionally containing W, Sb, Ni and/or Mo at atomic ratios of 0.0025 to 1:1 to vanadium.

Many references disclosing oxidation catalysts which are suitable for producing maleic anhydride by the partial oxidation of n-butane, which catalysts contain molybdenum as one component of a vanadium, phosphorus mixed oxide catalyst. For example U.S. Pat. No. 3,980,585 discloses a catalyst containing P, V Cu and one of Te, Zr, Ni, Ce, W, Pd, Ag, Mn, Cr, Zn, Mo, Re, Sn, La, Hf, Ta, Th, Ca, U or Sn; and U.S. Pat. No. 4,056,487 discloses a VPO catalyst containing Nb, Cu, Mo, Ni, Co and plus one or more of Ce, Nd, Ba, Hf, U, Ru, Re, Li or Mg. U.S. Pat. No. 4,515,904 discloses a procedure for preparing VPO catalysts which may include one metal of Mo, Zn, W, U, Sn, Bi, Ti, Zr, Ni, Cr or Co in atomic ratios of metal: V of 0.001 to 0.2:1.

U.S. Pat. No. 4,418,003 discloses VPO catalysts containing either Zn or Mo which is deactivated by Na or Li and which may also contain Zr, Ni, Ce, Cr, Mn, Ni and Al.

In any of the methods of preparation, heat may be applied to accelerate the formation of the complex.

PREFERRED CATALYSTS

A preferred catalyst is that produced from an alcoholic HCl solution reduction of vanadium pentoxide wherein the organic solvent is an alcohol and the reduction of the vanadium is obtained by contacting it with HCl. This is conveniently carried out by passing gaseous HCl through the alcohol having the vanadium pentoxide suspended therein. The vanadium pentoxide is reduced by the HCl and brought into solution as the vanadyl chloride. The completion of the reduction is the appearance of a dark reddish brown solution. Hydrogen bromide would be about the same as a reducing agent in this system. It is preferred that the reduction temperature should be maintained at no greater that 60° C. and preferably less than 55° C. Optimally active catalyst are the result when the reduction is carried out at temperatures in the range of about 35° C. to 55° C., preferably 40° C. to 55° C.

Generally in the catalyst preparation from 2500 to 4400 ml of alcohol, preferably 3100 to 4200 ml per pound of $V_2O_5$ and from 1.5 to 3.0 pounds of HCl per pound of $V_2O_5$ are employed.

To obtain the mixed oxides of vanadium and phosphorus, phosphoric acid of approximately 99% $H_3PO_4$ (98 to 101%) is added, for example, prepared from 85% $H_3PO_4$ and $P_2O_5$ or commercial grades of 105 and 115% phosphoric acid diluted with 85% $H_3PO_4$ and the vanadium compound digested which is discerned by a change in the color of the solution to a dark blue green. The digestion of the vanadium compound in the phosphoric acid is conducted at reflux until the color change indicated the completed digestion. Prior to the first reflux a minor portion, 1–5% by volume of the alcohol solvent is distilled out of the reaction solution. The remaining alcohol is stripped off in two stages to obtain the dried catalyst. Each of the two stages comprise refluxing the solvent for about 15 minutes to 10 hours, preferably about an hour followed by stripping of about 20–85 vol. % of the solvent after the first stage refluxing step and about 40–85 vol. % of the solvent remaining after the second refluxing step. Solvent remaining after the two stripping steps is removed by drying under less rigorous conditions.

The final removal of alcohol is usually carried out in an oven temperature in the range of 110° to 170° C. Reduced pressure can also be applied to lower oven temperatures. Generally calcination or roasting of the dried catalyst will be at a temperature in the range of 200° to 400° C. for a sufficient period to improve the catalytic properties of the composition. Preferably the crystallization occurs under static conditions which allows for more uniform conditions for crystal growth. The preferred catalysts are produced by the process comprising reducing vanadium in the +5 valence state in a substantially anhydrous organic medium to a valence of less than +5 and digesting said reduced vanadium in concentrated phosphoric acid wherein the improvement comprises (1) refluxing the solvent for a first period, (2) removing a portion of the solvent by distillation to initiate crystallization, (3) refluxing the solvent again for a second period during which the crystallization is substantially completed and (4) removing the remainder of the solvent. The use of a cosolvent system has been found to be beneficial.

The temperatures employed are relatively low hence the term calcination may not be appropriate. In any event, heating the composition under these temperature conditions has been found beneficial. The calcination is preferably carried out to produce materials having a characteristic powder x-ray diffraction ratio. The organic solvent is preferably a primary or secondary alcohol such as methanol, ethanol, 1-propanol, 2-propanol, butanol, 2-butanol, 2,methyl-1-propanol, 3-methyl-2-butanol, 2,2-dimethyl-1-propanol, 1-hexanol, 4-methyl-1-pentanol, 1-heptanol, 4 -methyl-1-hexanol, 4-methyl-1-heptanol, 1,2-ethanediol, glycerol, trimethylopropane, 4-methyl 2-pentanone, diethylene glycol and triethylene glycol or mixtures thereof. The alcohol is also a mild reducing agent for the vanadium +5 compound. A preferred cosolvent system comprises 2-butanol and from 5–50 vol. % of the cosolvent, e.g. isobutanol.

Generally the atomic ratio of Zn to vanadium is in the range of 0.001 to 0.15:1, however it has been found that lower ratios of zinc/vanadium produce the most active catalyst and compositions containing Zn/V mole ratio in the range of 0.01 to 0.07 are preferred.

The phosphorus is generally present in these catalyst as well as those of the prior art in the mole ratio of P/V 0.09–1.3/1. Optimum ratios P/V are found to be below 1.22/1 and above 1.0/1. The stabilizing effect of Mo allows the use of less phosphorus than otherwise comparable prior art catalyst and the concomitant benefit that phosphorus loss and the resulting deactivation of the catalyst in reactor operation is reduced, i.e., longer time trend (reactivity vs hours on stream).

The lithium component is present at an atomic ratio of 0.001 to 0.15:1, Li:V.

The point at which the zinc component, lithium component and molybdenum component is added is not critical so long as it is present prior to formation of the solid catalyst precipitate containing from 0.005 to 0.025 atoms of molybdenum per atom of vanadium. This is conveniently done along with the phosphoric acid addition, thereby assuring the intimate mixing of the catalyst component.

The modifier components are added as the compounds thereof such as acetates, carbonates, chlorides, bromides, oxides, hydroxides, phosphates and the like e.g., zinc chloride, zinc oxide, zinc oxalate, lithium acetate, lithium chloride, lithium bromide, lithium carbonate, lithium oxide, lithium orthophosphate, molybdenum oxide, molybdenum dioxydichloride, molybdenum dioxydibromide and the like.

The resultant catalyst complex is characterized as a mixed oxide, however, the structure of the complex has not been determined but may be conveniently represented by a formula such as:

$V\, P_a\, Zn_b\, Mo_c\, Li_d\, O_x$ a is 0.90 to 1.3, b is 0.001 to 0.15, c is 0.005 to 0.025 and d is 0.001 to 0.15. This representation is not an empirical formula and has no significance other than representing the atom ratio of the components of the catalyst. The x in fact, has no determinate value and can vary widely depending on the combinations within the complex. That there is oxygen present is known, and the $O_x$ is representative of this.

The catalyst may be employed as pellets, disc, flakes, wafers, or any other convenient shape which will facilitate its use in the tubular reactors employed for this type of vapor phase reaction. For example the catalyst may be prepared as tablets having a hole or bore therethrough as disclosed in U.S. Pat. No. 4,283,307 which is incorporated herein. The material can be deposited on a carrier. Although fixed bed tubular reactors are standard for this type of reaction, fluidized beds are frequently used for oxidation reactions, in which case the catalyst particle size would be on the order of about 10 to 150 microns.

OXIDATION PROCESS

The use of this class of catalyst for the partial oxidation of $C_4$–$C_{10}$ hydrocarbons to the corresponding anhydrides is generally recognized. They have been widely considered for the conversion of normal $C_4$ hydrocarbons, both the alkane, n-butane, and alkene, n-butene, for the production of maleic anhydride, which has a wide commercial usage.

The oxidation of the n-$C_4$ hydrocarbon to maleic anhydride may be accomplished by contacting, e.g., n-butane in low concentrations in oxygen with the described catalyst. Air is entirely satisfactory as a source of oxygen, but synthetic mixtures of oxygen and diluent gases, such as nitrogen, also may be employed. Air enriched with oxygen may be employed.

The gaseous feed stream to the standard tubular oxidation reactors normally will contain air and about 0.5 to about 2.5 mole percent hydrocarbons such as n-butane. About 1.0 to about 2.0 mole percent of the n-$C_4$ hydrocarbon are satisfactory for optimum yield of product for the process of this invention. Although higher concentrations may be employed, explosive hazards may be encountered except in fluidized bed reactors where concentrations of up to about 4 or 5 mole % can be used without explosive hazard. Lower concentrations of $C_4$, less than about one percent, of course, will reduce the total productivity obtained at equivalent flow rates and thus are not normally economically employed.

The flow rate of the gaseous stream through the reactor may be varied within rather wide limits but a preferred range of operations is at the rate of about 50 to 300 grams of $C_4$ per liter of catalyst per hour and more preferably about 100 to about 250 grams of $C_4$ per liter of catalyst per hour. Residence times of the gas stream will normally be less than about 4 seconds, more preferably less than about one second, and down to a rate where less efficient operations are obtained. The flow rates and residence times are calculated at standard conditions of 760 mm. of mercury and at 25° C. A preferred feed for the catalyst of the present invention for conversion to maleic anhydride is a n-$C_4$ hydrocarbon comprising a predominant amount of n-butane and more preferably at least 90 mole percent n-butane.

A variety of reactors will be bound to be useful and multiple tube heat exchanger type reactors are quite satisfactory. The tubes of such reactors may vary in diameter from about ¼ inch to about 3 inches, and the length may be varied from about 3 to about 10 or more feet. The oxidation reaction is an exothermic reaction and, therefor, relatively close control of the reaction temperature should be maintained. It is desirable to have the surface of the reactors at a relatively constant temperature and some medium to conduct heat from the reactors is necessary to aid temperature control. Such media may be Woods metal, molten sulfur, mercury, molten lead, and the like, but it has been found that eutectic salt baths are completely satisfactory. One such salt bath is a sodium nitrate-sodium nitrite-potassium nitrite eutectic constant temperature mixture. An additional method of temperature control is to use a metal block reactor whereby the metal surrounding the tube acts as a temperature regulating body. As will be recognized by one skilled in the art, the heat exchange medium may be kept at the proper temperature by heat exchangers and the like. The reactor or reaction tubes may be iron, stainless steel, carbon-steel, nickel, glass tubes such as Vycor and the like. Both carbon steel and nickel tubes have excellent long life under the conditions for the reactions described herein. Normally, the reactors contain a preheat zone of an inert material such as ¼ inch Alundum pellets, inert ceramic balls, nickel balls or chips and the like, present at about one-half to one-tenth the volume of the active catalyst present.

The temperature of reaction may be varied within some limits, but normally the reaction should be conducted at temperatures within a rather critical range. The oxidation reaction is exothermic and once reaction is underway, the main purpose of the salt bath or other media is to conduct heat away from the walls of the reactor and control the reactions. Better operations are normally obtained when the reaction temperature employed is no greater than about 100° C. above the salt bath temperature. The temperature in the reactor, of course, will also depend to some extent upon the size of the reactor and the $C_4$ concentration. Under usual operating conditions, in a preferred procedure, the temperature in the center of the reactor, measured by thermocouple, is about 365° C. to about 550° C. The range of temperature preferably employed in the reactor, measured as above, should be from about 380° C. to about 515° C. and the best results are ordinarily obtained at temperatures from about 390° C. to about 415° C. Described another way, in terms of salt bath reactors with carbon steel reactor tubes about 1.0 inch in diameter, the salt bath temperature will usually be controlled between about 350° C. to about 550° C. Under normal conditions, the temperature in the reactor ordinarily should not be allowed to go above about 470° C. for extended lengths of time because of decreased yields and possible deactivation of the catalyst.

Generally, the improved catalyst of the present invention is more active and operates at a lower temperature and higher weight yield then prior anhydrous process VPO catalysts.

The reaction may be conducted at atmospheric, super-atmospheric or below atmospheric pressure. The exit pressure will be at least slightly higher than the ambient pressure to insure a positive flow from the reaction. The pressure of the inert gases must be sufficiently high to overcome the pressure drop through the reactor.

The maleic anhydride may be recovered in a number of ways well known to those skilled in the art. For example, the recovery may be by direct condensation or by adsorption in suitable media, with subsequent separation and purification of the maleic anhydride.

The regeneration process of the present invention can generally be carried out by terminating the hydrocarbon feed and continuing the oxygen gas feed, e.g., air from the reaction at the temperature and pressure of the oxidation reaction with optimal steam at 0.1 to 5 vol. %. Preferably the regeneration process is carried out at a pressure of atmospheric up to 35 psi.

EXAMPLES

The following typical catalysts preparative procedures illustrate typical catalyst work up using the information discussed above. The crystallization carried on in the two reflux steps as described are easily controlled and reproduced to obtain the catalyst.

Example 1

Into a 12 liter round flask equipped with a mechanical stirrer, a gas inlet tube, thermowell, Dean stark trap with a condenser, and a heating mantle were charged 3564 ml anhydrous isobutanol and 627 grams $V_2O_5$. About 3.45 lb hydrogen chloride gas was bubbled into the stirred suspension. The reaction temperature was maintained at 40°±3° C. To the resulting dark red-brown solution was added 9.3 grams anhydrous zinc chloride, 2.92 grams lithium chloride, 17.67 grams 12-molybdophosphoric and a solution of phosphoric acid prepared from 193.7 grams $P_2O_5$ dissolved in 590 grams of 87.5% phosphoric acid. An additional 774 ml of anhydrous isobutanol were added to the reaction mixture. Heat was supplied and about 105 ml liquid were removed before the reaction mixture was placed under reflux conditions for 1 hour. After the first hour of reflux about 2460 ml solvent were removed by distillation. The slurry temperature was 111° C. at this stage. The distillation was stopped and the reaction mixture was refluxed for 1 hour during which the slurry temperature dropped to 108° C. At the start of the second reflux step a small amount of crystals were observed which acted as nucleation sites for the crystallization. At the end of the second reflux period most of the crystallization had been completed. The distillation was then resumed and was completed after about 1030 ml additional solvent was removed during which time the slurry temperature increased to 113° C. by the end of the distillation step. The thick slurry was dark green and not gummy and easy to handle and to recover. The thick slurry was then dried for 16 hours at 150° C. under air. The dry cake was then crushed and calcined in air at 260° C. for 3 hours. The calcined product had a 73% crystallinity by X-ray diffraction analysis. The calcined powder was mixed with 3% graphite and formed into $\frac{3}{16}"\times\frac{3}{16}"$ tablets with a hole struck therethrough.

The catalyst is conditioned for use by placing the catalyst (tablets) in the tubular reactor of a fixed bed reactor and carrying out the conditioning.

The reactor is 5 foot stainless steel tube, 1 inch outside diameter, packed with a 3.5 foot catalyst bed ($\frac{3}{16}"\times\frac{3}{16}"$ tablet with a $\frac{1}{16}"$ center hole) and with inert $\frac{1}{4}$ inch Alundum pellets on top of the catalyst material. The reactors are encased in a 7% sodium nitrate; 40% sodium nitrite; 53% potassium nitrite eutectic mixture constant temperature salt bath. The catalyst is loaded in the reactor and conditioned by a slow bring-up of the catalyst to operating temperature at the rate of 5° to 20° C. per hour achieved by heating the reactor and adjusting the gas flow from 0.5 to 1.5 mole % butane in air at an initial flow of GHSV of $900^{-1}$ hours up to $2500^{-1}$ hours while maintaining a desired conversion level, e.g., about 75 mole %, the procedure requiring in general several days. The initial temperature of the salt bath is about 250° C. (a point where the salt bath is molten).

The throughput is achieved in relation to the maximum salt bath temperature and maximum hot spot. The hot spot is determined by a probe through the center of the catalyst bed. The temperature of the salt bath can be adjusted to achieve the desired relationship between the conversion and flow rates of the n-$C_4$/air mixture (e.g. gas hourly space velocity–GHSV). The flow rate is adjusted to conversion and the temperature relations given above.

The C, S and Y used in reporting reaction results have the following meaning and relationship C(conversion)×S(selectivity)=Y(yield); where:

$$\% \text{ Conversion} = \frac{\text{moles n-butane reacted}}{\text{moles n-butane fed}} \times 100$$

$$\% \text{ Selectivity} = \frac{\text{moles maleic anhydride produced}}{\text{moles n-butane reacted}} \times 100$$

The term "weight yield" means the amount of maleic anhydride produced from a given amount of n-butene, calculated as follows:

$$\text{wt. \% yield} = \frac{98 \text{ (mole wt of maleic anhydride)}}{58 \text{ (mole wt of butane)}} \times \text{mole \% yld.}$$

Percent crystallinity is determined by comparing the intensity of the 2.94 d reflection of the dried catalyst material to that of a secondary standard of $VOHPO_4 \cdot \frac{1}{2}H_2O$.

After the catalyst had been on stream for about 1090 hours the butane feed was removed and the catalyst was treated at 430° C. with air for 8 hours. Thereafter the air was removed and the butane feed was reintroduced at 383° C. with 2500 GHSV.

The results from the testing are shown in TABLE I below. The results in TABLE 1 demonstrate that after air treatment the catalyst selectivity and MAN (maleic anhydride) yield increased and the hot spot temperature decreased by at least 6° C.

TABLE I[(1)]

| | EXAMPLE | | |
|---|---|---|---|
| | 1 Before Air | 2 | 3 |
| | | After Air Treatment | |
| Hours | 1090 | 1122 | 1290 |
| Salt °C. | 382 | 383 | 382 |
| Hot Spot °C. | 419 | 413 | 412 |
| GHSV, $HR_1$ | 2500 | 2500 | 2500 |
| % Butane | 1.31 | 1.30 | 1.31 |
| % Conversion | 80.5 | 79.5 | 80.0 |
| % Selectivity | 67.5 | 69.3 | 69.5 |
| Wt. % Yield | 91.7 | 93.0 | 93.8 |

[(1)] 1" × 5" Reactor; 3.5" bed with thermowell; $3/16$" × $3/16$" tablets with $1/16$" hole in center.

The invention claimed is:

1. A method for regenerating a vanadium/phosphorus mixed oxide oxidation catalyst having the formula $V P_a Zn_b Mo_c Li_d O_x$ wherein a is 0.90 to 1.3, b is 0.001 to 0.15, c is 0.005 to 0.025 and d is 0.001 to 0.15 which declines in activity to a first yield during use in the vapor phase production of maleic anhydride from n-$C_4$ hydrocarbons comprising passing a stream of substantially hydrocarbon free oxygen containing gas over the catalyst at a temperature in the range of 350° to 450° C. for 3 to 10 hours such that the catalyst exhibits a second yield of maleic anhydride greater than said first yield before regeneration.

2. The method according to claim 1 wherein said temperature is in the range of 400° to 430° C.

3. The method according to claim 1 wherein hydrocarbon is passed over said catalyst to produce maleic anhydride prior to passing said substantially hydrocarbon free oxygen containing gas.

4. The method according to claim 1 wherein hydrocarbon is passed over said catalyst to produce maleic anhydride after passing said substantially hydrocarbon free oxygen containing gas.

5. The method according to claim 1 wherein said oxygen containing gas comprises air.

6. The method according to claim 1 wherein said oxygen containing gas comprises 0.1 to 100 vol. % oxygen.

7. A method for regenerating a vanadium/phosphorus mixed oxide oxidation catalyst having the formula $V P_a Zn_b Mo_c Li_d O_x$ wherein a is 0.90 to 1.3, b is 0.001 to 0.15, c is 0.005 to 0.025 and d is 0.001 to 0.15 comprising the steps of:

a. contacting said catalyst with a stream of n-$C_4$ hydrocarbon in the presence of oxygen to produce maleic anhydride which declines to a first yield, b. terminating said stream of n-$C_4$ hydrocarbon, c. contacting said catalyst with a stream of oxygen containing air for a period of 3 to 10 hours to regenerate said catalyst and d. reintroducing said n-$C_4$ hydrocarbon to produce maleic anhydride at a second yield greater than said first yield before said regeneration.

8. The method according to claim 7 wherein said n-$C_4$ hydrocarbon comprises n-butane.

* * * * *